US009091697B2

(12) United States Patent
Trieu et al.

(10) Patent No.: US 9,091,697 B2
(45) Date of Patent: Jul. 28, 2015

(54) USE OF 2 ANTI-SPARC ANTIBODIES TO PREDICT RESPONSE TO CHEMOTHERAPY FOR PANCREATIC ADENOCARCINOMA

(71) Applicant: Abraxis BioScience, LLC, Los Angeles, CA (US)

(72) Inventors: Vuong Trieu, Agoura Hills, CA (US); Neil Desai, Los Angeles, CA (US); Daniel Knauer, Fairfield, NJ (US)

(73) Assignee: Abraxis BioScience, LLC, Los Angeles, CA (US)

( * ) Notice: Subject to any disclaimer, the term of this patent is extended or adjusted under 35 U.S.C. 154(b) by 3 days.

(21) Appl. No.: 13/775,980

(22) Filed: Feb. 25, 2013

(65) Prior Publication Data

US 2013/0172261 A1    Jul. 4, 2013

Related U.S. Application Data (63) Continuation of application No. 12/790,231, filed on May 28, 2010, now Pat. No. 8,383,358.

(60) Provisional application No. 61/182,081, filed on May 28, 2009.

(51) Int. Cl.
| | | |
|---|---|---|
| *G01N 33/574* | (2006.01) | |
| *A61K 39/395* | (2006.01) | |
| *A61P 35/00* | (2006.01) | |
| *G01N 33/68* | (2006.01) | |
| *A61K 38/38* | (2006.01) | |
| *A61K 47/48* | (2006.01) | |

(52) U.S. Cl.
CPC ............ *G01N 33/6893* (2013.01); *A61K 38/38* (2013.01); *A61K 47/48284* (2013.01); *A61K 47/48884* (2013.01); *G01N 33/57484* (2013.01); *G01N 2800/52* (2013.01)

(58) Field of Classification Search
CPC ............ A61K 38/38; A61K 47/48284; A61K 2300/00; A61K 47/48884; C12Q 1/6886; C12Q 2600/158; C12Q 2600/118; C12Q 2600/138; G01N 2800/52; G01N 33/57484; G01N 33/574; G01N 33/57407; B82Y 5/00
See application file for complete search history.

(56) References Cited

U.S. PATENT DOCUMENTS

| | | | |
|---|---|---|---|
| 4,816,567 A | 3/1989 | Cabilly et al. | |
| 5,003,621 A | 3/1991 | Gailus | |
| 5,821,337 A | 10/1998 | Carter et al. | |
| 2007/0184439 A1 | 8/2007 | Guilford et al. | |
| 2010/0069298 A1 | 3/2010 | Penny et al. | |

FOREIGN PATENT DOCUMENTS

| | | |
|---|---|---|
| AU | 2006249235 A1 | 1/2007 |
| CA | 2 774 550 A1 | 3/2011 |
| CN | 1867679 A | 11/2006 |
| CN | 101014720 A | 8/2007 |
| JP | 2006-517926 A | 8/2006 |
| JP | 2007-531500 A | 11/2007 |
| WO | 2004/064785 A2 | 8/2004 |
| WO | 2005/010213 A2 | 2/2005 |
| WO | 2005/017183 A2 | 2/2005 |
| WO | 2008/060651 A2 | 5/2008 |

OTHER PUBLICATIONS

Sato et al., SPARC/osteonectin is a frequent target for aberrant methylation in pancreatic adenocarcinoma and a mediator of tumor-stromal interactions. Oncogene, 22, 5021-5030, 2003.*
Kelly et al., *J. Leukoc. Biol.*, 81(3), 748-756 (2007).
Japanese Patent Application No. 513301/2012, Search Report (Jun. 10, 2014).
Chinese Patent Application No. 201080029187.8 Search Report (Sep. 23, 2013).
JP 513301/2012 Office Action (May 7, 2013).
Bellahcène et al., *Am. J. Pathol.*, 146 (1), 95-100 (1995).
Bradshaw et al., *PNAS*, 100 (10), 6045-6050 (May 13, 2003).
Catalog Entry, Anti-SPARC Antibody, R&D Systems Catalog, p. 691 (2007).
Chlenski et al., *Cancer Res.*, 62, 7357-7363 (Dec. 15, 2002).
Dhanesuan et al., *Br. Cancer Res. Treat.*, 75, 73-85 (2002).
Greenwald et al., *Adv. Drug Del. Rev.*, 55, 217-250 (2003).
Grønborg et al., *Molecular & Cellular Proteomics*, 5 (1), 157-171 (Jan. 2006).
Harlow, Ed and David Lane, *Using Antibodies: A Laboratory Manual*, Chapter 11, Cold Spring Harbor, NY, Cold Spring Harbor Laboratory Press (1999).
Infante et al., *J. Clin. Oncol.*, 25 (3), 319-325 (Jan. 20, 2007).
Jacob et al., *Cancer Res.*, 59, 4453-4457 (Sep. 1, 1999).
Jones, et al., *Drug Discovery Today*, 17, 232-241 (Mar. 2012).
Kaufmann et al., *Glycobiology*, 14 (7), 609-619 (2004).
Kim et al., *J. Korean Med. Sci.*, 13, 652-657 (1998).
Lane et al., *FASEB J.*, 8, 163-173 (1994).
Ledda et al., *Nature Med.*, 3 (2), 171-176 (Feb. 1997).
Mason et al., *EMBO J.*, 5 (7), 1465-1472 (1986).
Porter et al., *J. Histochem. & Cytochem.*, 43 (8), 791-800 (1995).
Rempel et al., *Clin. Cancer Res.*, 5, 237-241 (Feb. 1999).
Swaroop et al., *Genomics*, 2, 37-47 (1988).
Tai et al., *J. Clin. Invest.*, 115 (6), 1492-1502 (Jun. 2005).
Yamanaka et al., *J. Urol.*, 166, 2495-2499 (Dec. 2001).
Yan et al., *J. Histochem. & Cytochem.*, 47 (12), 1495-1505 (1999).
Yardley et al., *J. Clin. Oncol., ASCO Ann. Meeting Proceedings*, 27 (15S), 527 (May 20, 2009).
Yiu et al., *Am. J. Pathol.*, 159, 609-622 (2001).

* cited by examiner

*Primary Examiner* — Elly-Gerald Stoica
(74) *Attorney, Agent, or Firm* — Leydig, Voit & Mayer, Ltd.

(57) ABSTRACT

The invention provides anti-SPARC antibody-based techniques for predicting a response to chemotherapy.

3 Claims, 1 Drawing Sheet

USE OF 2 ANTI-SPARC ANTIBODIES TO PREDICT RESPONSE TO CHEMOTHERAPY FOR PANCREATIC ADENOCARCINOMA

RELATED APPLICATIONS

This application is a continuation of U.S. patent application Ser. No. 12/790,231, filed on May 28, 2010, which claims the benefit of U.S. Provisional Patent Application No. 61/182,081, filed on May 28, 2009, both of which are hereby incorporated by reference in their entirety.

BACKGROUND OF THE INVENTION

Secreted protein acidic and rich in cysteine (also known as osteonectin, BM40, or SPARC) (hereinafter "SPARC"), is a matrix-associated protein that elicits changes in cell shape, inhibits cell-cycle progression, and influences the synthesis of extracellular matrix (Bradshaw et al., Proc. Nat. Acad. Sci. USA 100: 6045-6050 (2003)). The murine SPARC gene was cloned in 1986 (Mason et al., EMBO J. 5: 1465-1472 (1986)) and a full-length human SPARC cDNA was cloned and sequenced in 1987 (Swaroop et al., Genomics 2: 37-47 (1988)). SPARC expression is developmentally regulated, and is predominantly expressed in tissues undergoing remodeling during normal development or in response to injury. For example, high levels of SPARC protein are expressed in developing bones and teeth (see, e.g., Lane et al., FASEB J., 8, 163 173 (1994); Yan & Sage, J. Histochem. Cytochem. 47:1495-1505 (1999)).

SPARC is upregulated in several aggressive cancers, but is absent in the corresponding normal tissues (Porter et al., J. Histochem. Cytochem., 43, 791 (1995)). SPARC expression is induced among a variety of tumors (e.g., bladder, liver, ovary, kidney, gut, and breast). In bladder cancer, for example, SPARC expression has been associated with advanced carcinoma. Invasive bladder tumors of stage T2 or greater have been shown to express higher levels of SPARC relative to bladder tumors of stage T1 (or less superficial tumors), and a poorer prognosis (see, e.g., Yamanaka et al., J. Urology, 166, 2495 2499 (2001)). In meningiomas, SPARC expression has been associated only with invasive tumors (see, e.g., Rempel et al., Clincal Cancer Res., 5, 237 241 (1999)). SPARC expression also has been detected in 74.5% of in situ invasive breast carcinoma lesions (see, e.g., Bellahcene, et al., Am. J. Pathol., 146, 95 100 (1995)), and 54.2% of infiltrating ductal carcinoma of the breast (see, e.g., Kim et al., J. Korean Med. Sci., 13, 652 657 (1998)). SPARC expression also has been associated with frequent microcalcification in breast cancer (see, e.g., Bellahcene et al., supra), suggesting that SPARC expression may be responsible for the affinity of breast metastases for the bone.

Surprisingly, SPARC has also been shown to have anti-tumor activity in some systems. SPARC is a potent cell cycle inhibitor that arrests cells in mid-$G_1$ (Yan & Sage, J. Histochem. Cytochem. 47:1495-1505 (1999)) and the inducible expression of SPARC has been shown to inhibit breast cancer cell proliferation in an in vitro model system (Dhanesuan et al., Breast Cancer Res. Treat. 75:73-85 (2002)). Similarly, exogenous SPARC can reduce the proliferation of both HOSE (human ovarian surface epithelial) and ovarian cancer cells in a concentration-dependent manner. In addition, SPARC induces apoptosis in ovarian cancer cells. Further evidence for SPARC receptors present on cells such as ovarian epithelial cells has been report. It has been proposed that the binding of SPARC to its receptor is likely to trigger tissue-specific signaling pathways that mediate its tumor suppressing functions (Yiu et al., Am. J. Pathol. 159:609-622 (2001)). Purified SPARC has also been reported to potently inhibit angiogenesis and significantly impair neuroblastoma tumor growth in an in vivo xenograft model system (Chlenski et al., Cancer Res. 62:7357-7363 (2002)).

Cancer is now primarily treated with one or a combination of three types of therapies: surgery, radiation, and chemotherapy. Surgery generally is only effective for treating the earlier stages of cancer. For more than 50% of cancer individuals, by the time they are diagnosed they are no longer candidates for effective surgical treatment. Radiation therapy is only effective for individuals who present with clinically localized disease at early and middle stages of cancer, and is not effective for the late stages of cancer with metastasis.

Chemotherapy involves the disruption of cell replication or cell metabolism. Chemotherapy can be effective, but there are severe side effects, e.g., vomiting, low white blood cells (WBC), loss of hair, loss of weight and other toxic effects. Because of the extremely toxic side effects, many cancer individuals cannot successfully finish a complete chemotherapy regime. Chemotherapy-induced side effects significantly impact the quality of life of the individual and may dramatically influence individual compliance with treatment. Additionally, adverse side effects associated with chemotherapeutic agents are generally the major dose-limiting toxicity (DLT) in the administration of these drugs. For example, mucositis is one of the major dose limiting toxicity for several anticancer agents, including the antimetabolite cytotoxic agents 5-FU, methotrexate, and antitumor antibiotics, such as doxorubicin. Many of these chemotherapy-induced side effects if severe may lead to hospitalization, or require treatment with analgesics for the treatment of pain. Some cancer individuals die from the chemotherapy due to poor tolerance to the chemotherapy. The extreme side effects of anticancer drugs are caused by the poor target specificity of such drugs. The drugs circulate through most normal organs of individuals as well as intended target tumors. The poor target specificity that causes side effects also decreases the efficacy of chemotherapy because only a fraction of the drugs is correctly targeted. The efficacy of chemotherapy is further decreased by poor retention of the anti-cancer drugs within the target tumors.

Due to the severity and breadth of cancer, there is a great need for effective treatments of such diseases or disorders that overcome the shortcomings of surgery, chemotherapy, and radiation treatment. In particular, in view of the serious side effects associated with chemotherapy, there is a need to identify which tumors will or will not respond to chemotherapeutic regimens.

BRIEF SUMMARY OF THE INVENTION

The invention provides a method for predicting the response of a tumor in an animal to a chemotherapeutic regimen, or treating the animal with a chemotherapeutic regimen based on immunostaining of a histologic section of the tumor with one or more anti-SPARC antibodies.

In one aspect, the invention provides a method for predicting the response of a tumor in an animal to a chemotherapeutic regimen comprising: (a) applying a first anti-SPARC antibody to a histologic section of the tumor, wherein the first anti-SPARC antibody preferentially immunostains SPARC in tumor cells; (b) applying a second anti-SPARC antibody to the histologic section of (a) or a second histologic section of the tumor, wherein the second anti-SPARC antibody preferentially immunostains SPARC in fibroblasts; and (c) predicting a positive response to the chemotherapeutic regimen if the first anti-SPARC antibody and the second anti-SPARC antibody immunostain the histologic section or sections.

In another aspect, the invention provides a method for predicting the response of a tumor in an animal to a chemotherapeutic regimen comprising: (a) applying a first anti-SPARC antibody to a histologic section of the tumor, wherein the first anti-SPARC antibody preferentially immunostains SPARC in tumor cells; (b) applying a second anti-SPARC antibody to the histologic section of (a) or a second histologic section of the tumor, wherein the second anti-SPARC antibody preferentially immunostains SPARC in fibroblasts; and (c) predicting a positive response to the chemotherapeutic regimen if the second anti-SPARC antibody immunostains the histologic section or sections.

In another aspect, the invention provides a method for predicting the response of a tumor in an animal to a chemotherapeutic regimen comprising: (a) applying a first anti-SPARC antibody to a histologic section of the tumor, wherein the first anti-SPARC antibody recognizes a SPARC epitope recognized by monoclonal antibody MAB941; (b) applying a second anti-SPARC antibody to the histologic section of (a) or a second histologic section of the tumor, wherein the second antibody recognizes a SPARC epitope recognized by polyclonal antibody AF941; and (c) predicting a positive response to the chemotherapeutic regimen if the first anti-SPARC antibody and the second anti-SPARC antibody immunostain the histologic section or sections.

In a further aspect, the invention provides a method for predicting the response of a tumor in an animal to a chemotherapeutic regimen comprising: (a) applying a first anti-SPARC antibody to a histologic section of the tumor, wherein the first anti-SPARC antibody recognizes a SPARC epitope recognized by monoclonal antibody MAB941; (b) applying a second anti-SPARC antibody to the histologic section of (a) or a second histologic section of the tumor, wherein the second antibody recognizes an immunodominant SPARC epitope recognized by polyclonal antibody AF941; and (c) predicting a positive response to the chemotherapeutic regimen if the second anti-SPARC antibody immunostains the histologic section or sections.

In yet another aspect, the invention provides a method of treating a tumor in an animal with a chemotherapeutic regimen comprising: (a) applying a first anti-SPARC antibody to a histologic section of the tumor, wherein the first anti-SPARC antibody preferentially immunostains SPARC in tumor cells; (b) applying a second anti-SPARC antibody to the histologic section of (a) or a second histologic section of the tumor, wherein the second anti-SPARC antibody preferentially immunostains SPARC in fibroblasts; and (c) administering the chemotherapeutic regimen if the first anti-SPARC antibody and the second anti-SPARC antibody immunostain the histologic section or sections.

In another aspect, the invention provides a method of treating a tumor in an animal with a chemotherapeutic regimen comprising: (a) applying a first anti-SPARC antibody to a histologic section of the tumor, wherein the first anti-SPARC antibody recognizes a SPARC epitope recognized by monoclonal antibody MAB941; (b) applying a second anti-SPARC antibody to the histologic section of (a) or a second histologic section of the tumor, wherein the second antibody recognizes a SPARC epitope recognized by polyclonal antibody AF941; and (c) administering the chemotherapeutic regimen if the first anti-SPARC antibody and the second anti-SPARC antibody immunostain the histologic section or sections.

In still another aspect, the invention provides a method for predicting the response of a tumor in an animal to a chemotherapeutic regimen comprising: (a) applying an anti-SPARC antibody to a histologic section of the tumor, wherein the anti-SPARC antibody recognizes a SPARC epitope recognized by monoclonal antibody MAB941; (b) predicting a poor response to the chemotherapeutic regimen if the anti-SPARC antibody immunostains the histologic section or sections.

In another aspect, the invention provides a method for predicting the response of a tumor in an animal to a chemotherapeutic regimen comprising: (a) applying an anti-SPARC antibody to the histologic section of (a) or a second histologic section of the tumor, wherein the second antibody recognizes an immunodominant SPARC epitope recognized by polyclonal antibody AF941; and (b) predicting a positive response to the chemotherapeutic regimen if the anti-SPARC antibody immunostains the histologic section or sections.

In particular, the invention provides methods for predicting the response of the tumor to a chemotherapeutic regimen, wherein the tumor is a melanoma or a pancreatic carcinoma, and the chemotherapeutic regimen comprises administering an albumin bound nanoparticulate paclitaxel alone or in combination with one or more other agents. When the tumor is a pancreatic carcinoma, the chemotherapeutic regimen comprises administering an albumin bound nanoparticulate paclitaxel and gemcitabine. When the tumor is a melanoma, the chemotherapeutic regimen comprises administering an albumin bound nanoparticulate paclitaxel and carboplatin.

Any one of these methods provided by the invention include methods wherein the mammal is a human patient

DETAILED DESCRIPTION OF THE INVENTION

SPARC expression in the tumor is complex with many components exhibiting SPARC expression including the stroma, fibroblast, tumor, inflammatory cells, normal tissue, nerve tissue, and blood vessels. The present invention relates to the components of the total SPARC expression pattern which are thought to be responsible for SPARC's impact on prognosis. The invention provides a comprehensive approach to analyzing SPARC expression which is able to more accurately predict response to therapy in a broad spectrum of cancers.

As used herein, the term "tumor" refers to any neoplastic growth, proliferation or cell mass whether benign or malignant (cancerous), whether a primary site lesion or metastases. As used herein, the term "cancer" refers to a proliferative disorder caused or characterized by the proliferation of cells which have lost susceptibility to normal growth control. Cancers of the same tissue type usually originate in the same tissue, and may be divided into different subtypes based on their biological characteristics. Four general categories of cancers are carcinoma (epithelial tissue derived), sarcoma (connective tissue or mesodermal derived), leukemia (blood-forming tissue derived) and lymphoma (lymph tissue derived). Over 200 different types of cancers are known, and every organ and tissue of the body may be affected. Specific examples of cancers that do not limit the definition of cancer may include melanoma, leukemia, astrocytoma, glioblastoma, retinoblastoma, lymphoma, glioma, Hodgkins' lymphoma and chronic lymphocyte leukemia. Examples of organs and tissues that may be affected by various cancers include pancreas, breast, thyroid, ovary, uterus, testis, prostate, thyroid, pituitary gland, adrenal gland, kidney, stomach, esophagus or rectum, head and neck, bone, nervous system, skin, blood, nasopharyngeal tissue, lung, urinary tract, cervix, vagina, exocrine glands and endocrine glands. Alternatively, a cancer may be multicentric or of unknown primary site (CUPS).

As used herein, a "cancerous cell" refers to a cell that has undergone a transformation event and whose growth is no longer regulated to the same extent as before said transformation event.

As used herein, a "medicament" is a composition capable of producing an effect that may be administered to a patient or test subject. The effect may be chemical, biological or physical, and the patient or test subject may be human, or a non-human animal, such as a rodent or transgenic mouse. The composition may include small organic or inorganic molecules with distinct molecular composition made synthetically, found in nature, or of partial synthetic origin. Included in this group are nucleotides, nucleic acids, amino acids, peptides, polypeptides, proteins, or complexes comprising at least one of these entities, The medicament may be comprised of the effective composition alone or in combination with a pharmaceutically acceptable excipient.

As used herein, a "pharmaceutically acceptable excipient" includes any and all solvents, dispersion media, coatings, antibacterial, antimicrobial or antifungal agents, isotonic and absorption delaying agents, and the like that are physiologically compatible. The excipient may be suitable for intravenous, intraperitoneal, intramuscular, intrathecal or oral administration. The excipient may include sterile aqueous solutions or dispersions for extemporaneous preparation of sterile injectable solutions or dispersion. Use of such media for preparation of medicaments is known in the art.

As used herein, a "pharmacologically effective amount" of a medicament refers to using an amount of a medicament present in such a concentration to result in a therapeutic level of drug delivered over the term that the drug is used. This may be dependent on mode of delivery, time period of the dosage, age, weight, general health, sex and diet of the subject receiving the medicament. The determination of what dose is a "pharmacologically effective amount" requires routine optimization which is within the capabilities of one of ordinary skill in the art.

A cancer or cancerous cell may be described as "sensitive to" or "resistant to" a given therapeutic regimen or chemotherapeutic agent based on the ability of the regimen to kill cancer cells or decrease tumor size, reduce overall cancer growth (i.e. through reduction of angiogenesis), and/or inhibit metastasis. Cancer cells that are resistant to a therapeutic regimen may not respond to the regimen and may continue to proliferate. Cancer cells that are sensitive to a therapeutic regimen may respond to the regimen resulting in cell death, a reduction in tumor size, reduced overall growth (tumor burden) or inhibition of metastasis.

The terms "treating," "treatment," "therapy," and "therapeutic treatment" as used herein refer to curative therapy, prophylactic therapy, or preventative therapy. An example of "preventative therapy" is the prevention or lessening the chance of a targeted disease (e.g., cancer or other proliferative disease) or related condition thereto. Those in need of treatment include those already with the disease or condition as well as those prone to have the disease or condition to be prevented. The terms "treating," "treatment," "therapy," and "therapeutic treatment" as used herein also describe the management and care of a mammal for the purpose of combating a disease, or related condition, and includes the administration of a composition to alleviate the symptoms, side effects, or other complications of the disease, condition. Therapeutic treatment for cancer includes, but is not limited to, surgery, chemotherapy, radiation therapy, gene therapy, immunotherapy, alternative therapeutic regimens, and combinations thereof.

As used herein, the term "agent" or "drug" or "therapeutic agent" refers to a chemical compound, a mixture of chemical compounds, a biological macromolecule, or an extract made from biological materials such as bacteria, plants, fungi, or animal (particularly mammalian) cells or tissues that are suspected of having therapeutic properties. The agent or drug can be purified, substantially purified or partially purified. An "agent" according to the present invention, also includes a radiation therapy agent or a "chemotherapuetic agent."

As used herein, "chemotherapy" refers to the administration of at least one chemotherapy agent which is harmful to destroy cancerous cells. There are a myriad of such chemotherapy agents available to a clinician. Chemotherapy agents may be administered to a subject in a single bolus dose, or may be administered in smaller doses over time. A single chemotherapeutic agent may be used (single-agent therapy) or more than one agent may be used in combination (combination therapy). Chemotherapy may be used alone to treat some types of cancer. Alternatively, chemotherapy may be used in combination with other types of treatment, for example, radiotherapy or alternative therapies (for example immunotherapy) as described herein. Additionally, a chemosensitizer may be administered as a combination therapy with a chemotherapy agent.

As used herein, a "chemotherapeutic agent" or "anticancer drug" refers to a medicament that may be used to treat cancer, and generally has the ability to kill cancerous cells directly. Examples of chemotherapeutic agents include alkylating agents, antimetabolites, natural products, hormones and antagonists, and miscellaneous agents. Examples of alternate names are indicated in brackets. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl-triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-mercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel and docetaxel (Taxotere); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interlelukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin-releasing hormone analogs such as leuprolide. Examples of miscellaneous agents include thalidomide; platinum coordination complexes such as cisplatin (cis-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib. Alternate names and trade-names of these and additional examples of chemotherapeutic agents, and their methods of use including dosing and administration regimens, will be known to a person versed in the art. In particular, suitable chemotherapeutic agents for use in accordance with the invention include, without limitation, albumin-bound nanoparticulate paclitaxels.

Abraxane™, also known as ABI-007, is preferred chemotherapeutic agent. Abraxane™ is an albumin-bound nanoparticulate formulation of paclitaxel. The use of an albumin nanoparticulate as a vehicle results in the formation of a colloid when reconstituted with saline. Based on clinical studies, it has been shown that the use of Abraxane™ is characterized by reduced hypersensitivity reactions as compared with Taxol™ Accordingly, premedication is not required for patients receiving Abraxane™.

Another advantage of the albumin-nanoparticulate formulation is that by excluding toxic emulsifiers it is possible to administer higher doses of paclitaxel at more frequent intervals than is possible with Taxol™. The potential exists that enhanced efficacy could be seen in solid tumors as a consequence of (i) higher tolerable doses (300 mg/m$^2$), (ii) longer half-life, (iii) prolonged local tumor availability and/or (iv) sustained in vivo release Abraxane™.

As used herein, the term "radiotherapeutic regimen" or "radiotherapy" refers to the administration of radiation to kill cancerous cells. Radiation interacts with various molecules within the cell, but the primary target, which results in cell death is the deoxyribonucleic acid (DNA). However, radiotherapy often also results in damage to the cellular and nuclear membranes and other organelles. DNA damage usually involves single and double strand breaks in the sugar-phosphate backbone. Furthermore, there can be cross-linking of DNA and proteins, which can disrupt cell function. Depending on the radiation type, the mechanism of DNA damage may vary as does the relative biologic effectiveness. For example, heavy particles (i.e. protons, neutrons) damage DNA directly and have a greater relative biologic effectiveness. Electromagnetic radiation results in indirect ionization acting through short-lived, hydroxyl free radicals produced primarily by the ionization of cellular water. Clinical applications of radiation consist of external beam radiation (from an outside source) and brachytherapy (using a source of radiation implanted or inserted into the patient). External beam radiation consists of X-rays and/or gamma rays, while brachytherapy employs radioactive nuclei that decay and emit alpha particles, or beta particles along with a gamma ray.

Radiotherapy may further be used in combination chemotherapy, with the chemotherapeutic agent acting as a radiosensitizer. The specific choice of radiotherapy suited to an individual patient may be determined by a skilled person at the point of care, taking into consideration the tissue and stage of the cancer.

As used herein, the term "alternative therapeutic regimen" or "alternative therapy" may include for example, biologic response modifiers (including polypeptide-, carbohydrate-, and lipid-biologic response modifiers), toxins, lectins, anti-angiogenic agents, receptor tyrosine kinase inhibitors (for example Iressa™ (gefitinib), Tarceva™ (erlotinib), Erbitux™ (cetuximab), imatinib mesilate (Gleevec™), proteosome inhibitors (for example bortezomib, Velcade™); VEGFR2 inhibitors such as PTK787 (ZK222584), aurora kinase inhibitors (for example ZM447439); mammalian target of rapamycin (mTOR) inhibitors, cyclooxygenase-2 (COX-2) inhibitors, rapamycin inhibitors (for example sirolimus, Rapamune™); farnesyltransferase inhibitors (for example tipifarnib, Zarnestra); matrix metalloproteinase inhibitors (for example BAY 12-9566; sulfated polysaccharide tecogalan); angiogenesis inhibitors (for example Avastin™ (bevacizumab); analogues of fumagillin such as TNP-4; carboxyaminotriazole; BB-94 and BB-2516; thalidomide; interleukin-12; linomide; peptide fragments; and antibodies to vascular growth factors and vascular growth factor receptors); platelet derived growth factor receptor inhibitors, protein kinase C inhibitors, mitogen-activated kinase inhibitors, mitogen-activated protein kinase kinase inhibitors, Rous sarcoma virus transforming oncogene (SRC) inhibitors, histonedeacetylase inhibitors, small hypoxia-inducible factor inhibitors, hedgehog inhibitors, and TGF-β signalling inhibitors. Furthermore, an immunotherapeutic agent would also be considered an alternative therapeutic regimen. Examples include chemokines, chemotaxins, cytokines, interleukins, or tissue factor. Suitable immunotherapeutic agents also include serum or gamma globulin containing preformed antibodies; nonspecific immunostimulating adjuvants; active specific immunotherapy; and adoptive immunotherapy. In addition, alternative therapies may include other biological-based chemical entities such as polynucleotides, including antisense molecules, polypeptides, antibodies, gene therapy vectors and the like. Such alternative therapeutics may be administered alone or in combination, or in combination with other therapeutic regimens described herein. Alternate names and trade-names of these agents used in alternative therapeutic regimens and additional examples of agents used in alternative therapeutic regimens, and their methods of use including dosing and administration regimens, will be known to a physician versed in the art. Furthermore, methods of use of chemotherapeutic agents and other agents used in alternative therapeutic regimens in combination therapies, including dosing and administration regimens, will also be known to a person versed in the art.

In particular, suitable alternative therapeutic regimens include, without limitation, antibodies to molecules on the surface of cancer cells such as antibodies to Her2 (e.g., Trastuzumab), EGF or EGF Receptors, VEGF (e.g., Bevacizumab) or VEGF Receptors, CD20, and the like. The therapeutic agent may further comprise any antibody or antibody fragment which mediates one or more of complement activation, cell mediated cytotoxicity, inducing apoptosis, inducing cell death, and opsinization. For example, such an antibody fragment may be a complete or partial Fc domain.

As used herein, the term "histologic section" refers to a thin section of a tissue sample suitable for mounting on a microscope slide and staining with any suitable protocol. As used herein, "immunostaining a histologic section" refers to the staining of the cells and intracellular matrix of the histologic section resulting from the binding of antibodies to components of the cells are intracellular matrix. As used herein, to "predominantly" or "preferentially" stain a structure, e.g., a cancer cell over a fibroblast, the immunostaining of the preferentially stained structure in the histologic section should be of an intensity of 3/3 when observed microscopically by those of ordinary skill, well all other structures stain with only an intensity of 1/3 or show 0/3 (no) staining.

As used herein, the term "epitope" refers to the three-dimensional structure bound by an antibody, and in particular the amino acid sequence targeted by the antibody. As used herein, the term "epitope recognized by the MAB941 monoclonal antibody" refers to the amino acid sequence in SPARC bound by the MAB941 monoclonal anybody. (SPARC monoclonal antibody (R&D Systems, Minneapolis, Minn.), catalog #MAB941)

As used herein, "immunodominant epitopes" refers to the three-dimensional structures bound with the greatest collective avidity by buying the antibodies polyclonal antisera. In particular, the epitopes responsible for the pattern of staining in immunostaining protocol employing that polyclonal antisera. As used herein, the term "immunodominant SPARC epitopes recognized by the AF941 polyconal antibody refers" to the SPARC peptides and amino acid sequences found with the greatest avidity by the AF941 polyconal antisera. Accordingly, binding to and staining of these SPARC peptides and amino acid sequences results and the majority of immunostaining observed. (SPARC polyclonal antibody (R&D Systems, Minneapolis, Minn.), catalog #AF941)

By "antibodies" it is meant without limitation, monoclonal antibodies, polyclonal antibodies, dimers, multimers, multispecific antibodies (e.g., bispecific antibodies). Antibodies may be murine, human, humanized, chimeric, or derived from other species. An antibody is a protein generated by the immune system that is capable of recognizing and binding to a specific antigen. A target antigen generally has numerous binding sites, also called epitopes, recognized by CDRs on multiple antibodies. Each antibody that specifically binds to a different epitope has a different structure. Thus, one antigen may have more than one corresponding antibody.

An antibody includes a full-length immunoglobulin molecule or an immunologically active portion of a full-length immunoglobulin molecule, i.e., a molecule that contains an antigen binding site that immuno specifically binds an antigen of a target of interest or part thereof. Targets include, cancer cells or other cells that produce autoimmune antibodies associated with an autoimmune disease.

The immunoglobulins disclosed herein can be of any class (e.g., IgG, IgE, IgM, IgD, and IgA) or subclass (e.g., IgG1, IgG2, IgG3, IgG4, IgA1 and IgA2) of immunoglobulin molecule. The immunoglobulins can be derived from any species.

"Antibody fragments" comprise a portion of a full length antibody, which maintain the desired biological activity. "Antibody fragments" are generally the antigen binding or variable region thereof. Examples of antibody fragments include Fab, Fab', F(ab')2, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The monoclonal antibodies referenced herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567). Chimeric antibodies of interest herein include "primatized" antibodies comprising variable domain antigen-binding sequences derived from a non-human primate (e.g., Old World Monkey or Ape) and human constant region sequences.

"Antibody-dependent cell-mediated cytotoxicity" and "ADCC" refer to a cell-mediated reaction in which nonspecific cytotoxic cells that express Fc receptors (FcRs) (e.g., Natural Killer (NK) cells, neutrophils, and macrophages) recognize bound antibody on a target cell and subsequently cause lysis of the target cell. The primary cells for mediating ADCC, NK cells, express Fc.γ.RIII only, whereas monocytes express FcγRI, FcγRII and FcγRIII. To assess ADCC activity of a molecule of interest, an in vitro ADCC assay may be performed (U.S. Pat. Nos. 5,003,621; 5,821,337). Useful effector cells for such assays include peripheral blood mononuclear cells (PBMC) and Natural Killer (NK) cells.

An antibody which "induces cell death" is one which causes a viable cell to become nonviable. Cell death in vitro may be determined in the absence of complement and immune effector cells to distinguish cell death induced by antibody-dependent cell-mediated cytotoxicity (ADCC) or complement dependent cytotoxicity (CDC). Thus, the assay for cell death may be performed using heat inactivated serum (i.e., in the absence of complement) and in the absence of immune effector cells. To determine whether the antibody is able to induce cell death, loss of membrane integrity as evaluated by uptake of propidium iodide (PI), trypan blue or 7AAD can be assessed relative to untreated cells. Cell death-inducing antibodies are those which induce PI uptake in the PI uptake assay in BT474 cells.

An antibody which "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies).

As used herein, a "chemosensitizer" or "sensitizer" is a medicament that may enhance the therapeutic effect of a chemotherapeutic agent, radiotherapy treatment or alternative therapeutic regimen, and therefore improve efficacy of such treatment or agent. The sensitivity or resistance of a tumor or cancerous cell to treatment may also be measured in an animal, such as a human or rodent, by, e.g., measuring the tumor size, tumor burden or incidence of metastases over a period of time. For example, about 2, about 3, about 4 or about 6 months for a human and about 2-4, about 3-5, or about 4-6 weeks for a mouse. A composition or a method of treatment may sensitize a tumor or cancerous cell's response to a therapeutic treatment if the increase in treatment sensitivity or the reduction in resistance is about 10% or more, for example, about 30%, about 40%, about 50%, about 60%, about 70%, about 80%, or more, to about 2fold, about 3-fold, about 4-fold, about 5-fold, about 10-fold, about 15-fold, about 20-fold or more, compared to treatment sensitivity or resistance in the absence of such composition or method. The determination of sensitivity or resistance to a therapeutic treatment is routine in the art and within the skill of a person versed in the art.

The terms "'peptide," "polypeptide," and "protein" may be used interchangeably, and refer to a compound comprised of at least two amino acid residues covalently linked by peptide bonds or modified peptide bonds, for example peptide isosteres (modified peptide bonds) that may provide additional desired properties to the peptide, such as increased half-life. A peptide may comprise at least two amino acids. The amino acids comprising a peptide or protein described herein may also be modified either by natural processes, such as post-translational processing, or by chemical modification techniques which are well known in the art. Modifications can occur anywhere in a peptide, including the peptide backbone, the amino acid side-chains and the amino or carboxyl termini. It is understood that the same type of modification may be present in the same or varying degrees at several sites in a given peptide.

Diagnostic and Therapeutic Methods

The present invention provides diagnostic methods for predicting the response of a tumor in an animal to a chemotherapeutic regimen, wherein one or more anti-SPARC antibodies capable of preferentially immunostaining SPARC in tumor cells and/or SPARC in fibroblasts, are applied to one or more histologic section of the tumor. A response to the chemotherapeutic regimen can then be predicted based on the immunostaining observed in the histologic section(s).

In some embodiments, the invention provides a method comprising (a) applying a first anti-SPARC antibody to a histologic section of the tumor, wherein the first anti-SPARC antibody preferentially immunostains SPARC in tumor cells; (b) applying a second anti-SPARC antibody to the histologic section of (a) or a second histologic section of the tumor, wherein the second anti-SPARC antibody preferentially immunostains SPARC in fibroblasts; and (c) predicting a positive response to the chemotherapeutic regimen if the first anti-SPARC antibody and the second anti-SPARC antibody immunostain the histologic section or sections.

In other embodiments, the invention provides a method comprising (a) applying a first anti-SPARC antibody to a histologic section of the tumor, wherein the first anti-SPARC antibody preferentially immunostains SPARC in tumor cells; (b) applying a second anti-SPARC antibody to the histologic section of (a) or a second histologic section of the tumor, wherein the second anti-SPARC antibody preferentially immunostains SPARC in fibroblasts; and (c) predicting a positive response to the chemotherapeutic regimen if the second anti-SPARC antibody immunostains the histologic section to which it was applied.

In a further embodiment, the invention provides a method comprising (a) applying an anti-SPARC antibody to a histologic section of the tumor, wherein the anti-SPARC antibody preferentially immunostains SPARC in tumor cells; and (b) predicting a negative response to the chemotherapeutic regimen if the anti-SPARC antibody immunostains the histologic section or sections. More particularly, immunostaining of tumor cells by an anti-SPARC antibody which preferentially immunostains SPARC in tumor cells (such as MAB941 or another antibody recognizing a SPARC epitope recognized by MAB941) can predict a negative outcome. In preferred embodiments for predicting a negative response, the tumor is a pancreatic carcinoma and the chemotherapeutic regimen is nanoparticle albumin-bound paclitaxel alone or in combination with gemcitabine. However, it will be understood that any solid cancerous tumor can be evaluated according to this method.

In another aspect, the invention provides a method for treating a tumor in an animal with a chemotherapeutic regimen. In some embodiments, the method comprises (a) applying a first anti-SPARC antibody to a histologic section of the tumor, wherein the first anti-SPARC antibody preferentially immunostains SPARC in tumor cells; (b) applying a second anti-SPARC antibody to the histologic section of (a) or a second histologic section of the tumor, wherein the second anti-SPARC antibody preferentially immunostains SPARC in fibroblasts; and (c) administering a chemotherapeutic regimen to the animal if the first anti-SPARC antibody and the second anti-SPARC antibody immunostain the histologic section or sections.

In some embodiments, the first anti-SPARC antibody recognizes a SPARC epitope recognized by the MAB941 antibody. For example, the first anti-SPARC antibody can be the MAB941 antibody. However, it will be understood that other anti-SPARC antibodies capable of binding this epitope with specificity can also be used in the present invention. In some embodiments, the second anti-SPARC antibody recognizes a SPARC epitope recognized by the AF941 antibody, preferably the immunodominant SPARC epitope recognized by the AF941 antibody. For example, the second anti-SPARC antibody can be the AF941 antibody.

However, it will be understood that other anti-SPARC antibodies capable of binding this epitope with specificity can also be used in the present invention. Epitope mapping can be done using standard techniques known in the art. For example, the protocols from "Epitope Mapping," Chapter 11, in Using Antibodies by Ed Harlow and David Lane. Cold Spring Harbor Laboratory Press, Cold Spring Harbor, N.Y., USA, 1999, which are hereby incorporated by reference in their entirety. By mapping the epitopes, epitope-specific antibodies can be readily generated by standard techniques.

Suitable anti-SPARC antibodies can be identified using tissue microarrays to assay for the correct distribution of tumor and fibroblast SPARC staining. Tissue microarrays can be prepared using any method known to one of ordinary skill in the art. Monoclonal and polyclonal antibodies made by standard techniques known in the art can be used. Antibodies can also be prepared which have specificity for both tumor SPARC and fibroblast SPARC. A bispecific antibody or other antibody having dual specificity for epitopes identified herein is particularly preferred in the methods of the present invention.

Combination therapies contemplated in the present invention include, but are not limited to antibody administration, vaccine administration, administration of cytotoxic agents, natural amino acid polypeptides, nucleic acids, nucleotide analogues, and biologic response modifiers. Two or more combined compounds may be used together or sequentially. Examples of chemotherapeutic agents include alkylating agents, antimetabolites, natural products, hormones and antagonists, and miscellaneous agents. Examples of alkylating agents include nitrogen mustards such as mechlorethamine, cyclophosphamide, ifosfamide, melphalan (L-sarcolysin) and chlorambucil; ethylenimines and methylmelamines such as hexamethylmelamine and thiotepa; alkyl sulfonates such as busulfan; nitrosoureas such as carmustine (BCNU), semustine (methyl-CCNU), lomustine (CCNU) and streptozocin (streptozotocin); DNA synthesis antagonists such as estramustine phosphate; and triazines such as dacarbazine (DTIC, dimethyl triazenoimidazolecarboxamide) and temozolomide. Examples of antimetabolites include folic acid analogs such as methotrexate (amethopterin); pyrimidine analogs such as fluorouracin (5-fluorouracil, 5-FU, 5FU), floxuridine (fluorodeoxyuridine, FUdR), cytarabine (cytosine arabinoside) and gemcitabine; purine analogs such as mercaptopurine (6-niercaptopurine, 6-MP), thioguanine (6-thioguanine, TG) and pentostatin (2'-deoxycoformycin, deoxycoformycin), cladribine and fludarabine; and topoisomerase inhibitors such as amsacrine. Examples of natural products include vinca alkaloids such as vinblastine (VLB) and vincristine; taxanes such as paclitaxel (Abraxane™) and docetaxel (Taxotere™); epipodophyllotoxins such as etoposide and teniposide; camptothecins such as topotecan and irinotecan; antibiotics such as dactinomycin (actinomycin D), daunorubicin (daunomycin, rubidomycin), doxorubicin, bleomycin, mitomycin (mitomycin C), idarubicin, epirubicin; enzymes such as L-asparaginase; and biological response modifiers such as interferon alpha and interleukin 2. Examples of hormones and antagonists include luteinising releasing hormone agonists such as buserelin; adrenocorticosteroids such as prednisone and related preparations; progestins such as hydroxyprogesterone caproate, medroxyprogesterone acetate and megestrol acetate; estrogens such as diethylstilbestrol and ethinyl estradiol and related preparations; estrogen antagonists such as tamoxifen and anastrozole; androgens such as testosterone propionate and fluoxymesterone and related preparations; androgen antagonists such as flutamide and bicalutamide; and gonadotropin releasing hormone analogs such as leuprolide. Examples of miscellaneous agents include thalidomide; platinum coordination complexes such as cisplatin (czs-DDP), oxaliplatin and carboplatin; anthracenediones such as mitoxantrone; substituted ureas such as hydroxyurea; methylhydrazine derivatives such as procarbazine (N-methylhydrazine, MIH); adrenocortical suppressants such as mitotane (o,p'-DDD) and aminoglutethimide; RXR agonists such as bexarotene; and tyrosine kinase inhibitors such as imatinib.

It will be understood that in determining whether or not an anti-SPARC antibody immunostains a histologic section, i.e., whether or not a histologic section is SPARC-positive, is within the skill of one of ordinary skill in the art. In some embodiments, the level of immunostaining can be quantified using any method standard in pathology, such that any level of immunostaining over a predetermined level will be understood to constitute a SPARC-positive sample. For example, immunostaining can be evaluated on a scale of 0-3, wherein 0=negative (<5% of cells staining), 1=very weak, 2=moderate staining (i.e. 5-50% of cells showing weak to intermediate intensity staining in an appropriate subcellular distribution), 3=strong staining (i.e. 5% of cells showing very intense staining or >50% of cells showing weak to moderately intense staining, in an appropriate subcellular distribution). Preferably, when such a scale is used, a sample is determined to be SPARC-positive when the score is 3. In other embodiments, a sample can be determined to be SPARC-positive when the score is 2 or even 1. In other embodiments, the level of immunostaining can be determined qualitatively, e.g., through comparison to positive or negative control samples. For example, if a histologic section exhibits immunostaining equal to or greater than a sample previously or separately determined to be SPARC-positive, then the histologic section will be understood to be SPARC-positive. Similarly, if a histologic section exhibits immunostaining equal to or less than a sample previously or separately determined to be SPARC-negative, then the histologic section will be understood to be SPARC-negative. Likewise, one of ordinary skill in the art will be able to determine whether a histologic section exhibiting immunostaining between that of a known SPARC-positive sample and a known SPARC-negative sample should be characterized as SPARC-positive or SPARC-negative.

The scoring or qualitative evaluation of SPARC immunostaining can be used to predict a positive or negative response to the chemotherapeutic regimen. A positive response as predicted in the methods of the present invention includes but is not limited to pathological response (reduction in tumor size or burden), overall survival, or progression free survival as shown by an improvement of the metric by at least 5%, preferably by at least 10%, more preferably by at least 15%, even more preferably by at least 20%, most preferably by at least 25% or more. Alternatively, the metric shows an improvement by a statistically significant amount in comparison with no or prior or alternative therapy. The negative response includes, but is not limited to pathological progression, decreased overall survival or decreased progression free survival.

The tumor can be any type of tumor known to one of ordinary skill in the art. In preferred embodiments, the tumor is a solid cancerous tumor. Exemplary tumors that can be evaluated or treated in the present methods can include oral cavity tumors, pharyngeal tumors, digestive system tumors, the respiratory system tumors, bone tumors, cartilaginous tumors, bone metastases, sarcomas, skin tumors, melanoma, breast tumors, genital system tumors, urinary tract tumors, orbital tumors, brain and central nervous system tumors, gliomas, endocrine system tumors, thyroid tumors, esophageal tumors, gastric tumors, small intestinal tumors, colonic tumors, rectal tumors, anal tumors, liver tumors, gall bladder tumors, pancreatic tumors, laryngeal tumors, tumors of the lung, bronchial tumors, non-small cell lung carcinoma, small cell lung carcinoma, uterine cervical tumors, uterine corpus tumors, ovarian tumors, vulvar tumors, vaginal tumors, prostate tumors, prostatic carcinoma, testicular tumors, tumors of the penis, urinary bladder tumors, tumors of the kidney, tumors of the renal pelvis, tumors of the ureter, head and neck tumors, parathyroid cancer, Hodgkin's disease, Non-Hodgkin's lymphoma, multiple myeloma, leukemia, acute lymphocytic leukemia, chronic lymphocytic leukemia, acute myeloid leukemia, chronic myeloid leukemia and anal tumors. Estrogen-receptor positive (ER+) tumors are also preferred in the present methods. In most preferred embodiments, the tumor is a melanoma, a breast tumor, a head and/or neck tumor, or a pancreatic carcinoma.

Contemplated chemotherapeutic regimens can include any chemotherapeutic treatment or anticancer drug as listed above. In some embodiments, the chemotherapeutic regimen comprises a taxane. In preferred embodiments, the chemotherapeutic regimen comprises paclitaxel. In preferred embodiments, the chemotherapeutic regimen is selected according to the type of cancer and/or tumor. For example, when the tumor is a pancreatic carcinoma, the chemotherapeutic regimen comprises paclitaxel, preferably nanoparticulate albumin bound paclitaxel (Abraxane™) gemcitabine, or combinations thereof. When the tumor is melanoma, the chemotherapeutic regimen comprises paclitaxel, preferably nanoparticulate albumin bound paclitaxel (Abraxane™), carboplatin, or combinations thereof. When the tumor is estrogen-receptor positive, the chemotherapeutic regimen can comprise paclitaxel, preferably nanoparticulate albumin bound paclitaxel (Abraxane™), an estrogen antagonist or ER+ ablation therapy, or combinations thereof.

Methods in accordance with the invention include, e.g., combination therapies wherein the animal is also undergoing one or more cancer therapies selected from the group consisting of surgery, chemotherapy, radiotherapy, thermotherapy, immunotherapy, hormone therapy and laser therapy. The terms "co-administration" and "combination therapy" refer to administering to a subject two or more therapeutically active agents. The agents can be contained in a single pharmaceutical composition and be administered at the same time, or the agents can be contained in separate formulation and administered serially to a subject. So long as the two agents can be detected in the subject at the same time, the two agents are said to be co-administered.

The administration of the pharmaceutical compositions of the present invention can be accomplished via any suitable route including, but not limited to, intravenous, subcutaneous, intramuscular, intraperitoneal, intratumoral, oral, rectal, vaginal, intravesical, and inhalational administration, with intravenous and intratumoral administration being most preferred. The composition can further comprise any other suitable components, especially for enhancing the stability of the composition and/or its end use. Accordingly, there is a wide variety of suitable formulations of the composition of the invention. The following formulations and methods are merely exemplary and are in no way limiting.

The pharmaceutical compositions can also include, if desired, additional therapeutic or biologically-active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

The carrier typically will be liquid, but also can be solid, or a combination of liquid and solid components. The carrier desirably is physiologically acceptable (e.g., a pharmaceutically or pharmacologically acceptable) carrier (e.g., excipient or diluent). Physiologically acceptable carriers are well known and are readily available. The choice of carrier will be determined, at least in part, by the location of the target tissue and/or cells, and the particular method used to administer the composition.

Typically, such compositions can be prepared as injectables, either as liquid solutions or suspensions; solid forms suitable for using to prepare solutions or suspensions upon the addition of a liquid prior to injection can also be prepared; and the preparations can also be emulsified. The pharmaceutical formulations suitable for injectable use include sterile aqueous solutions or dispersions; formulations containing known protein stabilizers and lyoprotectants, formulations including sesame oil, peanut oil or aqueous propylene glycol, and sterile powders for the extemporaneous preparation of sterile injectable solutions or dispersions. In all cases the formulation must be sterile and must be fluid to the extent that easy syringability exists. It must be stable under the conditions of manufacture and storage and must be preserved against the contaminating action of microorganisms, such as bacteria and fungi. Solutions of the active compounds as free base or pharmacologically acceptable salts can be prepared in water suitably mixed with a surfactant, such as hydroxycellulose. Dispersions can also be prepared in glycerol, liquid polyethylene glycols, and mixtures thereof and in oils. Under ordinary conditions of storage and use, these preparations contain a preservative to prevent the growth of microorganisms.

Pharmaceutically acceptable salts include the acid addition salts (formed with the free amino groups of the protein) and which are formed with inorganic acids such as, for example, hydrochloric or phosphoric acids, or such as organic acids as acetic, oxalic, tartaric, mandelic, and the like. Salts formed with the free carboxyl groups also can be derived from inorganic bases such as, for example, sodium, potassium, ammonium, calcium, or ferric hydroxides, and such organic bases as isopropylamine, trimethylamine, histidine, procaine and the like.

Formulations suitable for parenteral administration include aqueous and non aqueous, isotonic sterile injection solutions, which can contain anti oxidants, buffers, bacteriostats, and solutes that render the formulation isotonic with the blood of the intended recipient, and aqueous and non aqueous sterile suspensions that can include suspending agents, solubilizers, thickening agents, stabilizers, and preservatives. The formulations can be presented in unit dose or multi dose sealed containers, such as ampules and vials, and can be stored in a freeze dried (lyophilized) condition requiring only the addition of a sterile liquid excipient, for example, water, for injections, immediately prior to use. Extemporaneous injection solutions and suspensions can be prepared from sterile powders, granules, and tablets of the kind previously described. In a preferred embodiment of the invention, the peptide ligand domain-containing conjugate is formulated for injection (e.g., parenteral administration). In this regard, the formulation desirably is suitable for intratumoral administration, but also can be formulated for intravenous injection, intraperitoneal injection, subcutaneous injection, and the like.

Formulations suitable for administration via inhalation include aerosol formulations. The aerosol formulations can be placed into pressurized acceptable propellants, such as dichlorodifluoromethane, propane, nitrogen, and the like. They also can be formulated as non pressurized preparations, for delivery from a nebulizer or an atomizer.

Formulations suitable for anal administration can be prepared as suppositories by mixing the active ingredient with a variety of bases such as emulsifying bases or water soluble bases. Formulations suitable for vaginal administration can be presented as pessaries, tampons, creams, gels, pastes, foams, or spray formulas containing, in addition to the active ingredient, such carriers as are known in the art to be appropriate.

In addition, the composition of the invention can comprise additional therapeutic or biologically active agents. For example, therapeutic factors useful in the treatment of a particular indication can be present. Factors that control inflammation, such as ibuprofen or steroids, can be part of the composition to reduce swelling and inflammation associated with in vivo administration of the pharmaceutical composition and physiological distress.

In the case of inhalational therapy, the pharmaceutical composition of the present invention is desirably in the form of an aerosol. Aerosol and spray generators for administering the agent if in solid form are available. These generators provide particles that are respirable or inhalable, and generate a volume of aerosol containing a predetermined metered dose of a medicament at a rate suitable for human administration. Examples of such aerosol and spray generators include metered dose inhalers and insufflators known in the art. If in liquid form, the pharmaceutical compositions of the invention can be aerosolized by any suitable device.

When used in connection with intravenous, intraperitoneal or intratumoral administration, the pharmaceutical composition of the invention can comprise sterile aqueous and non-aqueous injection solutions, suspensions or emulsions of the active compound, which preparations are preferably isotonic with the blood of the intended recipient. These preparations can contain one or more of anti-oxidants, buffers, surfactants, cosolvents, bacteriostats, solutes which render the compositions isotonic with the blood of the intended recipient, and other formulation components known in the art. Aqueous and non-aqueous sterile suspensions can include suspending agents and thickening agents. The compositions can be presented in unit-dose or multi-dose containers, for example sealed ampoules and vials.

The invention also provides, if desirable, embodiments in which the peptides are administered as "alternative therapies" and such peptides may be conjugated to polyethylene glycol (PEG). PEG conjugation can increase the circulating half-life of these polypeptides, reduce the polypeptide's immunogenicity and antigenicity, and improve their bioactivity. If used, any suitable method of PEG conjugation can be used, including but not limited to, reacting methoxy-PEG with a peptide's available amino group(s) or other reactive sites such as, e.g., histidines or cysteinees. In addition, recombinant DNA approaches can be used to add amino acids with PEG-reactive groups to the peptide ligand domain-containing conjugate. Further, releasable and hybrid PEG-ylation strategies can be used in accordance with the aspects of the present invention, such as the PEG-ylation of polypeptide, wherein the PEG molecules added to certain sites in the peptide ligand domain-containing conjugatemolecule are released in vivo. Examples of PEG conjugation methods are known in the art. See, e.g., Greenwald et al., Adv. Drug Delivery Rev. 55:217-250 (2003).

The animal can be any patient or subject in need of treatment or diagnosis. In preferred embodiments, the animal is a mammal. In particularly preferred embodiments, the animal is a human. In other embodiments, the animal can be a mouse, rat, rabbit, cat, dog, pig, sheep, horse, cow, or a non-human primate.

The following examples further illustrate the invention but, of course, should not be construed as in any way limiting its scope.

EXAMPLE 1

This example describes analysis of patient responsiveness to Abraxane™ albumin-bound nanoparticulate paclitaxel in view of retrospective tumor SPARC status.

Fifty-four patients with head and neck cancer were treated with intra-arterial Abraxane™ albumin-bound nanoparticulate paclitaxel, and their tumors were measured radiographically to determine responsiveness to treatment. Retroactively, the tumor SPARC status was determined for 16 patients for whom such data was available.

For all patients (n=54), overall positive response to Abraxane™ albumin-bound nanoparticulate paclitaxel was 45/54 (78%). For patients with known tumor SPARC status, 10 of 12 patients (83%) having SPARC-positive tumors responded to Abraxane™. In contrast, for patients having SPARC-negative tumors, only 1 out of 4 patients (25%) responded with such treatment. Results are significant to P=0.06 using the Fisher exact test.

These results show a likely correlation between tumor SPARC positive status and responsiveness to Abraxane™ albumin-bound nanoparticulate paclitaxel chemotherapy.

EXAMPLE 2

This example describes the identification of the different components of SPARC expression in the tumor microenvironement and their use in providing prognostic information.

A series of antibodies against SPARC were evaluated for their binding characteristics in a range of normal and tumor tissues. The SPARC expression pattern, as determined by immunostaining, in various components of tumors was determined including the SPARC expression levels in tumor cells, blood vessels, fibroblast, stroma, inflammatory cells, and the adjacent normal tissues. Two antibodies were identified with differential affinity for SPARC and were employed in follow up studies. Specifically, the pattern of staining was determined using a monoclonal antibody ("antibody M") (SPARC monoclonal antibody (R&D Systems, Minneapolis, Minn.), catalog #MAB941 Lot # ECH045011 diluted 1:100 in a tris based diluent) and a polyclonal antibody ("antibody P") (SPARC polyclonal antibody (R&D Systems, Minneapolis, Minn., catalog #AF941 Lot # EWN04 diluted 1:50 in a tris based diluents).

Histologic sections of tumors were prepared on slides and stained using a standard immunostaining protocol. Briefly, tissue cores from formalin-fixed, paraffin-embedded tumor blocks (2 cores from the most representative areas per block) were arrayed (Beecher Instruments, Silver Spring, Md.) to create a tissue microarray of cores measuring 2.0 mm each and were placed on positively charged slides. Slides with specimens were then placed in a 60° C. oven for 1 hour, cooled, deparaffinized, and rehydrated through xylenes and graded ethanol solutions to water. All slides were stained using automated staining equipment (Dako Cytomation Autostainer, Dako, Carpinteria, Calif.).

All slides were quenched for 5 minutes in a 3% hydrogen peroxide solution in water to block for endogenous peroxidase. After a buffer rinse, slides were incubated with antibody M or a negative control reagent for 30 minutes. A mouse horseradish peroxidase polymer kit (Mouse MACH 3 HRP Polymer Kit, Biocare Medical, Concord, Calif.) was incubated for 20 minutes per reagent. After another buffer rinse, DAB chromogen (Dako, Carpinteria, Calif.) was applied for 10 minutes. Hematoxylin was used to counterstain the slides. The same protocol was used for immunostaining specimens with antibody P, although an avidin-biotin detection kit (Biocare Medical, Concord, Calif.), incubated for 15 minutes per reagent, was used in place of the HRP detection kit.

Detailed pathological evaluation of SPARC expression in a series of tumors was performed by a board certified pathologist. The level of SPARC expression, as determined by immunohistochemistry, was scored for different tumor components. Scores were assigned to the level of SPARC expression on scale of 0-3, with 3 being the most positive score, as is commonly done in the art and well known to those of ordinary skill in the art. The monoclonal and polyclonal antibodies used detected different patterns of SPARC expression as shown in Table 1.

TABLE 1

| | Tumor | | Fibroblast | |
|---|---|---|---|---|
| | Antibody P | Antibody M | Antibody P | Antibody M |
| Breast | 30/106 | 35/106 p = ns | 82/107 | 26/107 p < 0.0001 |
| Pancreas | 20/36 | 7/36 p = 0.0031 | 18/29 | 5/29 p = 0.0011 |
| Melanoma | 30/41 | 20/41 p = 0.0408 | 19/33 | 14/33 p = ns |

The polyclonal antibody demonstrated preferential staining of SPARC in fibroblasts. While the monoclonal anybody preferably stained SPARC in tumor cells. From these staining preferences the following SPARC patterns were analyzed for their predictive value in a series of tumors:

A, when 3+ was found in any of the components.

B, when 3+ was found in any of the components with the monoclonal anti-SPARC antibody.

C, when 3+ was found in any of the components with the monoclonal anti-SPARC antibody.

D, when 3+ was found in tumor cells with both anti-SPARC antibodies.

E, when 3+ was found in fibroblasts with both anti-SPARC antibodies.

Logistic regression and proportional hazard were used to determine the correlation between response, progression-free survival ("PFS") and overall survival ("OS") to the SPARC pattern.

Figure 1:
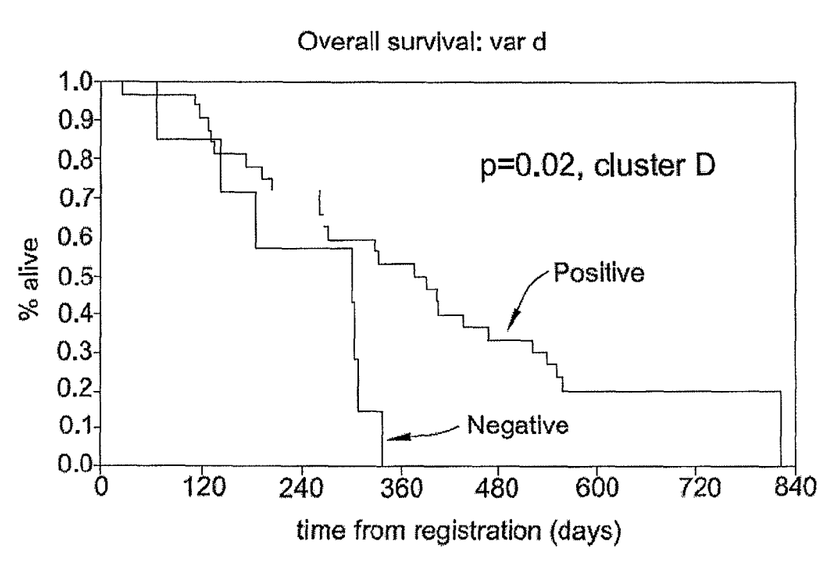
FIG. 1 shows the melanoma overall survival curve.

One of the tumor sets was a phase II trial of carboplatin and nab-paclitaxel (ABI-007) in patients with unresectable stage 1V melanoma. Specifically, nab-paclitaxel (100 mg/m$^2$) and Carboplatin (AUC2) were administered on days 1, 8, and 15 of a 28 day cycle. As shown in FIG. 1 there was a statistically significant correlation between the D pattern (i.e., when 3+ was found in tumor cells with both anti-SPARC antibodies) and overall survival.

Another set of tumors was obtained from patients with advanced pancreatic adenocarcinoma who had been treated with Abraxane™ albumin-bound nanoparticulate paclitaxel (100-150 m g/m$^2$) and Gencitabine (1000 mg/m$^2$) given on days 1, 8, and 15 of a 28-day cycle. Among these patients, responses to treatment were observed as shown in Table 2.

TABLE 2

| | Response | | | |
|---|---|---|---|---|
| | CR* | PR* | SD* | PD* |
| N of 32 pts | 2 (6%) | 14 (44%) | 14 (44%) | 2 (6%) |

(*CR, Complete Response; PR, Partial Response; SD, Stable Disease; PD, Progressive Disease)

Among these patients of there was significant correlation between response and SPARC expression in tumor cells as determined by staining with the polyclonal anti-SPARC antibody (one tail t-test, p=0.027). On the other hand, staining of the tumor cells with the monoclonal antibody predicted a worse overall survival and progression free survival.

In addition, B patterned staining (i.e., when 3+ was found in any of the components with the monoclonal anti-SPARC antibody) was predictive of the worst progression free survival on this regimen in these patients with pancreatic adenocarcinoma.

These results show a statistically significant relationship between patient responses to nanoparticulate paclitaxel based regimens (specifically, Abraxane® based regimens) and the pattern of SPARC expression in the different cell types of the tumor.

EXAMPLE 3

This example evaluates whether SPARC expression has any correlation with estrogen receptor (ER) positivity in breast cancer.

Fifty-four ER positive (ER+) and 52 ER negative (ER-) breast tumor samples from two neo-adjuvant breast trials were evaluated with the two anti-SPARC antibody combination. Staining of the tumor cells with the monoclonal anti-SPARC antibody significantly correlated with ER positivity (p=0.01). Of the 54 ER+ tumors, 44.44% (n=24) were mAT SPARC positive, while 55.58% (n=30) were SPARC negative. Of the 52 ER-tumors, 78.5% (n=41) were also SPARC negative, while 21.15% (n=11) were SPARC positive.

While ER positivity is thought to be a good prognostic indicator in breast cancer, these results demonstrate that it is also associated with SPARC positivity.

EXAMPLE 4

This example provides an exemplary protocol for the preparation and immunologic staining of histologic sections.

Tissue cores from formalin-fixed, paraffin-embedded tumor blocks (2 cores from the most representative areas per block) are arrayed (Beecher Instruments, Silver Spring, Md.) to create a tissue microarray of cores measuring 2.0 mm each and are placed on positively charged slides. Slides with specimens are placed in a 60° C. oven for 1 hour, cooled, deparaffinized, and rehydrated through xylenes and graded ethanol solutions to water. All slides are quenched for 5 minutes in a 3% hydrogen peroxide solution in water to block for endogenous peroxidase. Antigen retrieval is performed by a heat method in which the specimens were placed in a citric acid solution, pH 6.1 (code S1699, Dako, Carpinteria, Calif.) for 20 minutes at 94° C. using a vegetable steamer, then cooled for 15 minutes. Slides are then placed on an immunostaining system such as the Dako Cytomation Autostainer (Dako, Carpinteria, Calif.) for use with immunohistochemistry utilizing suitable antibodies.

This method is based on the consecutive application of (1) a primary antibody against the antigen to be localized, (2) biotinylated linking antibody, (3) enzyme-conjugated streptavidin, and (4) substrate chromogen (DAB). Slides are then counterstained in Richard-Allan hematoxylin (Kalamazoo, Mich.), dehydrated through graded ethanol solutions, and topped with a coverslip.

EXAMPLE 5

This example provides an exemplary protocol for the preparation and immunologic staining of histologic sections using multiple immunostains simultaneously ("2-color double immunostain").

As in Example 4 above, paraffin-embedded tissue blocks are cut at 4 µm and placed on positively charged slides. Slides with specimens are then placed in a 60° C. oven for 1 hour, cooled, deparaffinized, and rehydrated through xylenes and graded ethanol solutions to water. All slides are then quenched for 5 minutes in a 3% hydrogen peroxide solution in water to block for endogenous peroxidase. Antigen retrieval is performed by a heat method in which the specimens are placed in a citric acid solution (pH 6.1) for 25 minutes (as compared with 20 minutes for the individual antibodies mentioned previously) at 94° C. and cooled for 15 minutes using a vegetable steamer. Slides are then placed on an immunostaining system (Dako, Carpinteria, Calif.), for use with immunhistochemistry.

The first primary antibody is incubated for 30 minutes at room temperature. The detection system, EnVision+ dual link (Dako, code K4061, Carpinteria, Calif.), is incubated for 30 minutes. Lastly, DAB chromogen. Before the second primary antibody is applied, serum-free protein block is added (Dako, code X0909, Carpinteria, Calif.) to minimize background and crossover between primary antibodies. The second primary antibody is incubated for 1 hour at room temperature. The EnVision+ dual link (Dako, code K4061, Carpinteria, Calif.) is used again as the detection system and incubated for 30 minutes. NovaRED (Vector Laboratories, Burlingame, Calif.) is used with the second primary antibody so that the staining by the two antibodies can be easily differentiated. Slides are then counterstained in Richard-Allan hematoxylin, dehyrated through graded ethanol solutions, and topped with a coverslip.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a pancreatic adenocarcinoma in an animal with a chemotherapeutic regimen comprising paclitaxel and gemcitabine, wherein said method comprises:
   (a) obtaining histologic sections from a tumor resulting from the pancreatic adenocarcinoma,
   (b) applying a first anti-SPARC antibody to a first histologic section of the tumor, wherein the first anti-SPARC antibody preferentially immunostains SPARC in tumor cells and wherein the first anti-SPARC antibody recognizes a SPARC epitope recognized by monoclonal antibody MAB941;
   (c) applying a second anti-SPARC antibody to the first histologic section of (a) or a second histologic section of the tumor, wherein the second anti-SPARC antibody preferentially immunostains SPARC in fibroblasts and wherein the second anti-SPARC antibody recognizes an immunodominant SPARC epitope recognized by polyclonal antibody AF941
   (d) determining whether the first anti-SPARC antibody immunostains any component of the tumor;
   (e) determining whether the second anti-SPARC antibody immunostains any component of the tumor; and
   (f) treating the animal by
      (i) administering the chemotherapeutic regimen if the tumor cells of the pancreatic adenocarcinoma are immunostained with the second anti-SPARC antibody, but not the first anti-SPARC antibody and the immunostaining by the first anti-SPARC antibody of any other component of the tumor has an intensity of 2+ or less;
      (ii) not administering the chemotherapeutic regimen if first anti-SPARC antibody immunostains the tumor cells or immunostains any other component of the tumor with an intensity of 3+; and
      (iii) not administering the chemotherapeutic regimen if second anti-SPARC antibody does not stain the tumor cells.

2. The method of claim 1, wherein the chemotherapeutic regimen comprises nanoparticulate, albumin bound paclitaxel.

3. The method of claim 1, wherein the animal is a human patient.

* * * * *